United States Patent
Bajgrowicz et al.

Patent Number: 5,929,291
Date of Patent: Jul. 27, 1999

[54] ODORANTS

[75] Inventors: Jerzy A. Bajgrowicz, Zürich; Georg Frater, Winterthur, both of Switzerland

[73] Assignee: Givaudan Roure (International) SA, Vernier-Geneve, Switzerland

[21] Appl. No.: 08/842,930

[22] Filed: Apr. 9, 1997

[30] Foreign Application Priority Data

Apr. 9, 1996 [EP] European Pat. Off. .............. 96105555
Apr. 10, 1996 [EP] European Pat. Off. .............. 96105603

[51] Int. Cl.$^6$ .................................................. C07C 35/22
[52] U.S. Cl. .............................. 568/819; 512/19; 512/25; 568/374; 568/379; 568/445; 568/446; 568/838; 568/816
[58] Field of Search .................... 568/816, 819, 568/838; 512/19, 25

[56] References Cited

U.S. PATENT DOCUMENTS

| | | |
|---|---|---|
| 4,052,341 | 10/1977 | Naipawer et al. . |
| 4,610,813 | 9/1986 | Schulte-Elte et al. . |
| 4,696,766 | 9/1987 | Naipawer . |

FOREIGN PATENT DOCUMENTS

| | | |
|---|---|---|
| 155 591 A2 | 3/1985 | European Pat. Off. . |
| 243 021 | 2/1987 | Germany . |
| 266 347 | 3/1989 | Germany . |
| WO 92/22518 | of 1992 | WIPO . |

OTHER PUBLICATIONS

K. Schulze, et al. *Liebigs Ann. Chem.* (1993) 987–991.
K. Schulze, et al. *J. Prakt. Chem.* (1993) 335;687–693.
A.S. Dimoglo, et al. *New J. Chem.* (1995) 19;149–154.
Chemical Abstracts, vol. 102(21); May 27, 1985.
Comprehensive Organic Synthesis, Ed. Trost B.M., Fleming I., Pergamon Press, Oxford, England 1991, vol. 2, p. 133 seq.
Comprehensive Organic Synthesis, Ed. Trost B.M., Fleming I., Pergamon Press, Oxford, England 1991, vol. 1, p. 755 seq.
Comprehensive Organic Synthesis, Ed. Trost B.M., Fleming I., Pergamon Press, Oxford, England 1991, vol. 8, p. 242 seq.
Comprehensive Organic Synthesis, Ed. Trost B.M., Fleming I., Pergamon Press, Oxford, England 1991, vol. 8, 1 seq.
Comprehensive Organic Synthesis, Ed. Trost B.M., Fleming I., Pergamon Press, Oxford, England 1991, vol. 4, p. 951 seq.
Comprehensive Organic Synthesis, Ed. Trost B.M., Fleming I., Pergamon Press, Oxford, England 1991, vol. 5, p. 999 seq.
Comprehensive Organic Synthesis, Ed. Trost B.M., Fleming I., Pergamon Press, Oxford, England 1991, vol. 4, p. 987.
Comprehensive Organic Synthesis, Ed. Trost B.M., Fleming I., Pergamon Press, Oxford, England 1991, vol. 3, p. 21 seq.
Comprehensive Organic Synthesis, Ed. Trost B.M., Fleming I., Pergamon Press, Oxford, England 1991, vol. 4, p. 69 seq.
Comprehensive Organic Synthesis, Ed. Trost B.M., Fleming I., Pergamon Press, Oxford, England 1991, vol. 8, p. 523 seq.
Protective Groups in Organic Synthesis, Greene T., Wuts P.G.M., John Wiley & Sons Inc., New York 1991, p. 175 seq.
Protective Groups in Organic Synthesis, Greene T., Wuts P.G.M., John Wiley & Sons Inc., New York 1991, p. 10 seq.

*Primary Examiner*—Michael L. Shippen
*Attorney, Agent, or Firm*—Mark E. Waddell; Bryan Cave LLP

[57] ABSTRACT

The invention relates to compounds of the general formula

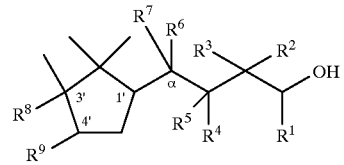

I in which $R^1$ to $R^7$ are, independently, H, methyl or ethyl, $R^8$+$R^9$ together form methylene (—$CH_2$—) or a single bond, or $R^1$+$R^2$ together form —$(CH_2)_n$—, with n being 3 or 4, or $R^3$+$R^5$ or $R^5$+$R^7$ represent methylene or a single bond; and the presence of at least one cyclopropane ring in the molecule is compulsory and the side chain can be saturated or contains one double bond in position α,β or β,γ a process for the manufacture of these compounds, compounds used to perform the process and the use of these compounds as an odorant or as an ingredient of an odorant composition.

24 Claims, No Drawings

ODORANTS

The invention relates to novel odorants derived from campholenic aldehyde. In particular these are compounds of the general formula

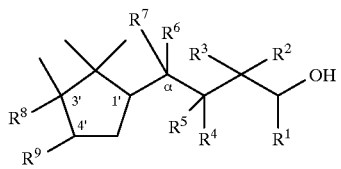

I in which $R^1$ to $R^7$ are, independently, H, methyl or ethyl, $R^8+R^9$ together form methylene (—$CH_2$—) (i.e., forming a cyclopropane ring at the 3', 4' position of the cyclopentane ring) or a single bond (thus resulting in a double bond between 3' and 4' positions), or $R^1+R^2$ together form —$(CH_2)_n$—, with n being 3 or 4, or $R^3+R^5$ or $R^5+R^7$ together form methylene or a single bond; and the presence of at least one cyclopropane ring in the molecule is compulsory and the side chain can be saturated or contains one double bond in position $\alpha,\beta$ or $\beta,\gamma$.

The novel compounds I may be obtained by a process comprising a) mono- or dicyclopropanating a compound of formulae

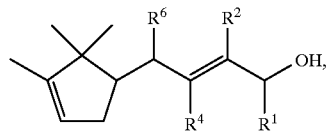

IIa

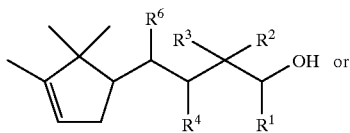

IIb

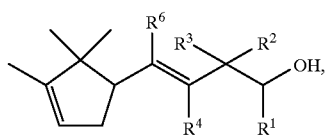

IIc or b) reducing a compound of formulae

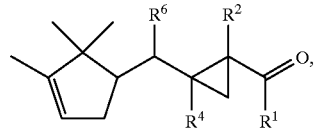

1

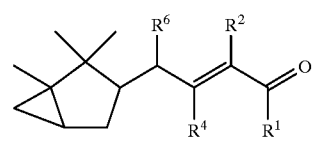

3

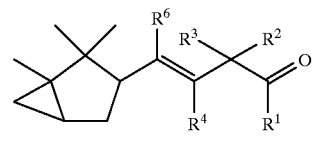

4 in a manner known per se, and, if desired, hydrogenating any double bond present in the compound I thereby obtained.

Possible routes to these novel compounds I starting from campholenic aldehyde and passing through the compounds II–IV are outlined in reaction schemes 1 and 2 hereafter.

The scheme 2 also shows a preferred route to the intermediate compound IV.

For the sake of clarity these two schemes do not include the optional alcohol protection and deprotection steps which can, preferably, be effected before and after cyclopropanation (steps e) and f) respectively).

Scheme 1. Access to cyclopropanated campholenic aldehyde derivatives Ia–e

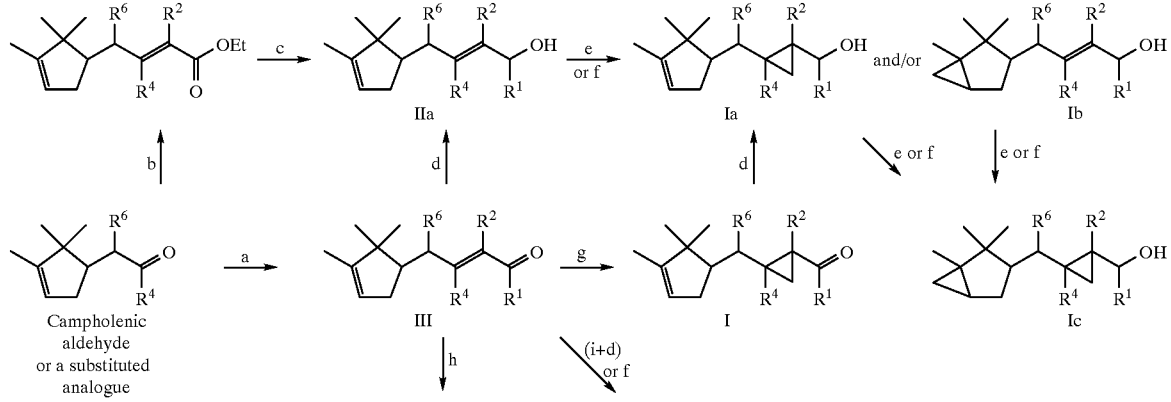

-continued

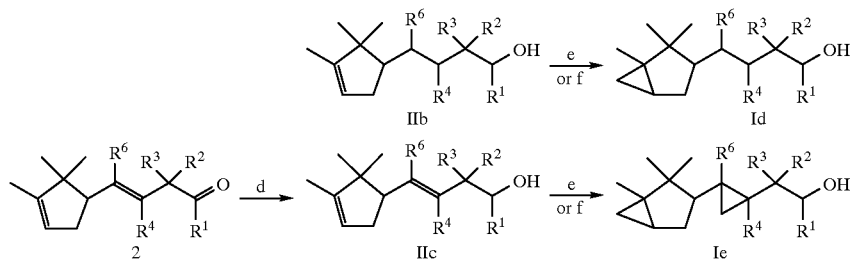

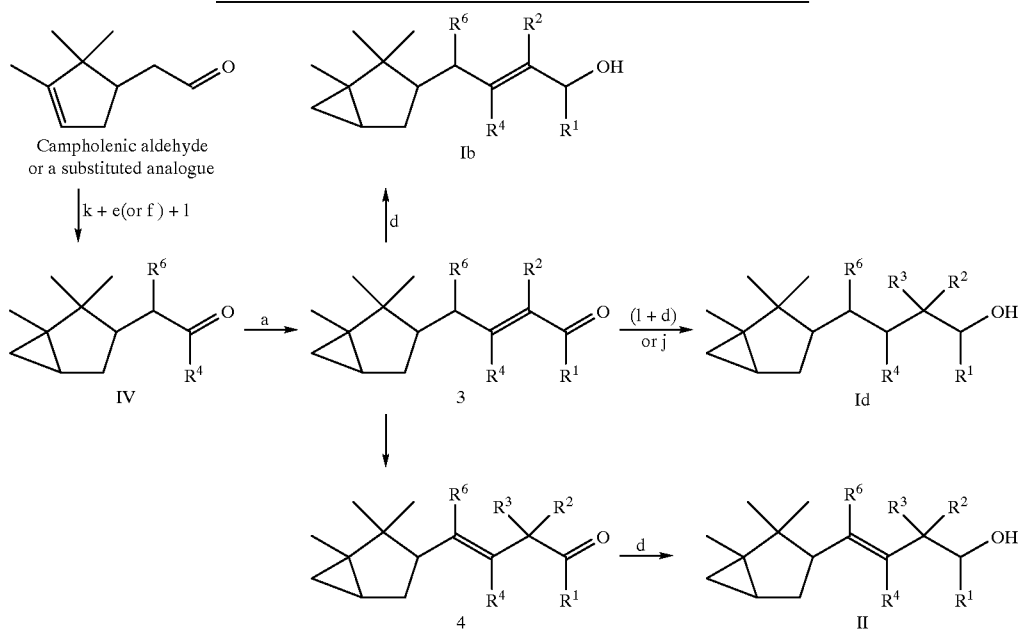

Scheme 2. Access to cyclopropanated campholenic aldehyde derivatives Ib, d, f

As shown in these schemes, the route from the known intermediates makes use of known chemical transformations. These are:

a) aldol condensation, effecting elongation of the side chain, e.g. by reacting campholenic aldehyde with the reactant $R^2CH_2C(O)R^1$ under basic conditions, e.g. using any organic or inorganic base, b) Wittig-Horner alkenation of aldehydes and ketones using phosphoranes or phosphonates, e.g. triethylphosphonoacetate, c) reduction of carboxylic esters to alcohols, e.g. using hydrides, e.g. $LiAlH_4$ in ether solvents, d) reduction of carbonyl groups to saturated and unsaturated alcohols, e.g. using hydrides, e.g. borohydrides, e.g. $NaBH_4$ in alkanols, e) cyclopropanation of C=C double bonds via methylene transfer, e.g. according to Simmon-Smith, e.g. using $CH_2X_2$, X being I or Br, and a metal (e.g. zinc-copper or zinc-silver) couple or diethylzinc or trialkyl aluminium etc., optionally in the presence of an activator such as acetyl bromide, $TiCl_4$ or ultrasound, f) cyclopropanation by formation of and reductive dehalogenation of 1,1-dihalocyclopropanes, e.g. with $CHX_3$ (X=Cl,Br) and a base, conveniently under phase transfer conditions, or with an alkali metal salt or an alkyl ester of trichloroacetic acid and at elevated temperatures, followed by a reduction using, e.g. an alkali metal e.g. in THF or in ethanol, etc. Steps e) and f) lead to mono- and dicyclopropanated products depending on the reaction conditions and the relative reactivity of the C=C double bonds of IIa, g) cyclopropanation of C=C double bonds of $\alpha,\beta$-enones using ylides, e.g. using dimethylsulfonium or dimethyloxosulfonium methylide with or without solvent (e.g. THF, $CH_2Cl_2$, DMS, etc.), h) deconjugation or deconjugative alkylation of $\alpha,\beta$-enones, e.g. by providing first basic conditions, then reacting with $R^3X$ (X=Cl, Br, I) or $H^+$, or, in the case of deconjugation, using an acid, or metal based catalysts, i) conjugated addition of organometallics to $\alpha,\beta$-enones, leading to $\beta$-substituted carbonyl compounds, e.g. by the couple MeMgBr/CuI, conveniently in an ether as solvent, j) reduction of $\alpha,\beta$- or $\beta,\gamma$-enones to saturated alcohols, e.g. by catalytic hydrogenation, such as $H_2$/Pt, using any inert organic solvent, k) protection of the aldehyde function, e.g. as a dioxolane, before cyclopropanation, l) deprotection of the aldehyde function following cyclopropanation, e.g. using a strong acid, such as HCl/SiO$_2$, m) protection and deprotection of the alcohol function, preferably in steps e) and f), e.g. as esters, ethers, silyl ethers, etc., see Protective Groups in Organic Synthesis, T. Greene, P. G. M. Wuts, John Wiley & Sons, Inc. New York, 1991.

As pointed out above, these transformations as exemplified in the experimental part are known and their principles described in detail, e.g. in Comprehensive Organic Synthesis, Ed. Trost B. M., Fleming I., Pergamon Press, Oxford, England 1991 (for a–h) and in Protective Groups in Organic Synthesis, Greene T., Wuts P. G. M., John Wiley & Sons Inc., New York, 1991 (for the protection/deprotection steps): namely in a) vol 2, p 133 seq.
b) vol 1, p 755 seq.
c) vol 8, p 242 seq.
d) vol 8, p 1 seq.
e) vol 4, p 951 seq.
f) vol 4, p 999 seq.
g) vol 4, p 987
h) vol 3, p 21 seq.
i) vol 4, p 69 seq.
j) vol 8, p 523 seq.
k) p 175 seq.
l) p 175 seq.
m) p 10 seq.

Campholenic aldehyde is a most important starting material for the synthesis of synthetic odorants exhibiting the odor profile of sandalwood oil (see, e.g. U.S. Pat. Nos. 4,052,341, 4,696,766).

No campholenic aldehyde derived cyclopentylbutanols or pentanols bearing a cyclopropane ring have however been published up to now.

Adding one or two such cyclopropane rings on campholenic aldehyde derivatives modifies in particular the odor and substantivity (i.e. persistence of the odor) of the new derivatives. The new alcohols of the general formula I exhibit various woody odor aspects; most of them exert a sandalwood odor, but some are also just woody/amber-like.

Among the novel compounds, [1-methyl-2-(1,2,2-trimethyl-bicyclo-[3.1.0]hex-3-ylmethyl)cyclopropyl] methanol has the most natural, the strongest and most persistent sandalwood odor, superior to any existing synthetic (commercial) raw materials exhibiting sandalwood odor. All four stereoisomers of this compound contribute to its overall natural creamy, flowery, woody odor, but one of the (3"R)-diastereomers was found to constitute the main odor vector, approximatively 34 times more powerful than the second strongest among the synthesized stereoisomers.

The new cyclopropanated carbonyl compounds 1, 3, 4 as well as the new derivatives of the general formula IIb (with R$^4$=Me) exhibit also useful olfactory properties, their odor belonging also to the amber/woody/ sandalwood family of odors.

The present invention thus comprises also the compounds I, IIb, 3, 4 and their use as odorants, and a process to prepare compounds I.

The olfactory properties of the novel compounds harmonize with a multitude of natural or synthetic products widely used in compositions, in particular for generating middle and bottom notes, since the novel compounds are endowed with very good tenacity.

The compounds I harmonize particularly well with all floral notes, in particular with rose, iris, jasmine, ylang-ylang and narcissus notes. They also harmonize with balsamic or resinous dry-out notes such as styrax, incense, and benzoin, and woody notes, such as oak moss or tree moss, patchouli and vetiver.

They thus provide most distinguished mixtures with a multitude of natural and synthetic raw materials.

Examples are:

natural products, such as, for example, tree moss absolute, basil oil, tropical fruit oils (such as bergamot oil, mandarine oil, etc.), mastix absolute, myrtle oil, palmarosa oil, patchouli oil, petitgrain oil, wormwood oil, lavender oil, rose oil, jasmin oil or ylang-ylang oil etc.;

alcohols, such as farnesol, geraniol, linalool, nerol, phenylethyl alcohol, rhodinol, cinnamic alcohol, cis-3-hexenol, menthol, α-terpineol etc.;

aldehydes, such as citral, α-hexyl cinnamaldehyde, hydroxycitronellal, Lilial, (p-tert-butyl-α-methyl-dihydrocinnamaldehyde), methylnonylacetaldehyde, phenylacetaldehyde, anisaldehyde, vanillin etc.;

ketones, such as allylionone, α-ionone, β-ionone, isoraldein (isomethyl-α-ionone), verbenone, nootkatone, geranylacetone etc.;

esters, such as allyl phenoxyacetate, benzyl salicylate, cinnamyl propionate, citronellyl acetate, decyl acetate, dimethylbenzylcarbinyl acetate, ethyl acetoacetate, cis-3-hexenyl isobutyrate, linalyl acetate, methyl dihydrojasmonate, styrallyl acetate, vetiveryl acetate, benzyl acetate, cis-3-hexenyl salicylate, geranyl acetate etc.;

lactones, such as γ-undecalactone, 6-decalactone, pentadecan-15-olide (Exaltolid), 12-oxahexadecanolide (Hibiscolide), etc.;

acetals, such as Viridine (1,1-dimethoxy-2-phenylethane) etc.;

various components often used in perfumery, such as indole, p-menthane-8-thiol-3-one, methyleugenol, eugenol, anethol etc.

The percentages in which these derivatives are used may vary within wide limits ranging from a few parts per thousand in mass market products (e.g. cleaning, deodorant) up to a few per cent in alcoholic extracts for (fine) perfumery. "Overdoses" of up to 20% of these derivatives come also in consideration, and may thus impart very particular effects e.g. in combination with synthetic musks. However, even small amounts of the novel compounds provide the odorant compositions with a rich sandalwood or ambery/woody effect and increase the volume (strength and diffusivity) and substantivity of their odor.

There is really no restriction regarding the type of formulations and the destination of the actual finished product: thus, eau de cologne, toilet water, scented water, perfume, cream, shampoo, deodorant, soap, detergent powder, household cleaner, softener, etc. come into consideration.

The compounds I integrate into a multitude of compositions, e.g. oriental chypres, green and woody, floral leathers, fougere tobaccos and fruity aldehyde, etc. They provide, via their olfactory note, exceptional richness and linkage between the dry-out constituents of the compositions by providing more volume, warmth and roundness and augmenting sandalwood and woody aspects.

Except where otherwise stated, all the campholenic aldehyde derivatives used as intermediates in the following examples were obtained starting from a ~1:2 mixture of (S)-(−) and (R)-(+) campholenic aldehyde, both enantiomers being available from the suitable α-pinene. However, the general formula I should encompass both the pure isomers and mixtures of configurational, namely opticals isomers, see carbons (1',3',4',α,β,γ,δ) as well as the geometrical isomers (cis/trans isomerism), since all these isomers can be generated using the appropriate starting materials and synthetic methods.

The structure of the compounds described in the examples has been proven by their IR, NMR and mass spectra. All of them are colorless oils.

EXAMPLE 1

3-Methyl-5-(1,2,2-trimethylbicyclo[3.1.0]hex-3-yl)pentan-2-ol 34.6 g (0.13 mol) of diiodomethane was added to a stirred suspension of 17.0 g (0.26 mol) of zinc powder and 2.58 g (26 mmol) of cuprous chloride in 70 ml of anhydrous diethyl ether. The reaction mixture was sonicated for 30 minutes in a standard ultrasound bath. A solution of 21.0 g (0.10 mol) of 3-methyl-5-(2,2,3-trimethylcyclopent-3-enyl)-pentan-2-ol in 20 ml of the same solvent was added dropwise (exothermic reaction) and the sonication (reflux) continued for further 7 hours. The reaction mixture was poured into 330 ml of 1N hydrochloric acid and extracted with 300 ml of tert-butyl methyl ether. The organic layer was washed with 2×150 ml of brine, dried (MgSO$_4$) and concentrated in vacuo to give 29 g of brownish oil which after distillation using a 10 cm Vigreux column at 100–105° C./0.08 Torr and subsequent flash chromatography with 300 g of silica gel (eluent: hexane/MTBE 5:1) yielded 10.6 g (47% yield) of 3-methyl-5-(1,2,2-trimethylbicyclo[3.1.0]hex-3-yl)pentan-2-ol.

IR (neat): 3348, 3059, 2998, 2960, 2929, 2856, 1463, 1379, 1363, 1299, 1098, 1013, 924 cm$^{-1}$.

Odor: sandalwood, amber, woody, creamy.

EXAMPLE 2

2,3-Dimethyl-4-(1,2,2-trimethylbicyclo[3.1.0]hex-3-yl)butan-1-ol a) 2,3-dimethyl-4-(2,2,3-trimethylcyclopent-3-enyl)butanal 100 ml (0.30 mol) of methylmagnesium bromide solution in diethyl ether was added to 60.0 g (0.32 mol) of cuprous iodide suspended in 350 ml of the same solvent at −10° C., followed by addition of 52.0 g (0.27 mol) of 2-methyl-4-(2,2,3-trimethylcyclopent-3-enyl)but-2-enal dissolved in 300 ml of anhydrous diethyl ether at 0° C. and stirring at the same temperature was continued for 0.5 hours. The reaction mixture was treated with 200 ml of 1.0 N hydrochloric acid, decanted and the organic layer was washed with 2×300 ml of brine, dried (MgSO$_4$) and concentrated in vacuo. The residue was purified by flash chromatography on silica gel (eluent: hexane/MTBE 15:1) to give 28.2 g (50% yield) of 2,3-dimethyl-4-(2,2,3-trimethylcyclopent-3-enyl)butanal.

IR (neat): 3036, 2957, 2930, 2874, 2834, 2700, 1725, 1460, 1383, 1360, 1015, 798 cm$^{-1}$.

b) 2,3-dimethyl-4-(2,2,3-trimethylcyclopent-3-enyl)butan-1-ol

A solution of 18.0 g (86 mmol) of 2,3-dimethyl-4-(2,2,3-trimethylcyclopent-3-enyl)butanal in 50 ml of ethanol was added dropwise at 0° C. to 45.0 g (0.11 mol) of sodium borohydride suspended in 200 ml of the same solvent. After 18 hours of stirring at room temperature 100 ml of 1.0 N aqueous hydrochloric acid was added dropwise at 0° C. The reaction mixture was extracted with 200 ml of MTBE, the extract washed with with 3×100 ml of brine, dried (MgSO$_4$) and concentrated in vacuo. The residue was distilled at 82–86° C./0.1 Torr to give 14.1 g (78% yield) of 2,3-dimethyl-4-(2,2,3-trimethylcyclopent-3-enyl)butan-1-ol.

IR (neat): 3338, 3037, 2956, 2928, 2834, 1461, 1381, 1360, 1024, 798 cm$^{-1}$.

Odor: sandalwood, amber, fruity, floral.

c) 2,3-dimethyl-4-(1,2,2-trimethylbicyclo[3.1.0]hex-3-yl)butan-1-ol 1.0 g (3.7 mmol) of diiodomethane was added to the stirred suspension of 0.97 g (15 mmol) of zinc powder and 0.15 g (1.5 mmol) of cuprous chloride in 20 ml of anhydrous diethyl ether. The reaction mixture was sonicated for 15 minutes in a standard ultrasound bath, then 0.60 g (2.8 mmol) of 2,3-dimethyl-4-(2,2,3-trimethylcyclopent-3-enyl)butan-1-ol was added and the sonication (reflux) continued for further 2 hours. After addition of 1.68 g (6.3 mmol) more of diiodomethane followed by further 4 hours of sonication the reaction mixture was diluted with 50 ml of tert-butyl methyl ether and filtered over Celite. The filtrate was washed with 50 ml of 1N aqueous hydrochloric acid and 50 ml of brine, dried (MgSO$_4$) and concentrated in vacuo to give 1.3 g of brownish oil. The purification by flash chromatography on silica gel (eluent: hexane/ MTBE 4:1) gave 0.30 g (48% yield) of 2,3-dimethyl-4-(1,2,2-trimethylbicyclo[3.1.0]hex-3-yl)butan-1-ol.

IR (neat): 3335, 3036, 2955, 2928, 1462, 1381, 1360, 1115, 1024, 798 cm$^{-1}$.

Odor: woody, sandalwood, floral.

EXAMPLE 3

3,3-Dimethyl-5-(1,2,2-trimethylbicyclo[3.1.0]hex-3-yl)pentan-2-ol 7.5 g (33 mmol) of 3,3-dimethyl-5-(1,2,2-trimethylcyclopent-3-enyl)pentan-2-ol was treated according to Example 1 with 3.25 g (50 mmol) of zinc dust, 0.50 g (5 mmol) of cuprous chloride and 13.4 g (50 mmol) of diiodomethane except for shorter sonication time which was 20 minutes for the preparation of Zn/Cu couple and 4 hours for the cyclopropanation. Flash chromatography of the crude product (6.8 g of yellow oil) on 200 g of silica gel (eluent: hexane/MTBE 5:1) yielded 1.9 g (24% yield) of 3,3-dimethyl-5-(1,2,2-trimethyl-bicyclo[3.1.0]hex-3-yl)pentan-2-ol.

IR (neat): 3389, 3060, 2960, 2934, 2869, 1464, 1363, 1095, 1014, 911 cm$^{-1}$.

Odor: woody, sandalwood.

EXAMPLE 4

[1-Methyl-2-(1,2,2-trimethylbicyclo[3.1.0]hex-3-ylmethyl)cyclopropyl]methanol 200 g (1.15 mol) of dibromomethane and 1 ml (0.013 mol) of acetyl bromide were added successively to a suspension of 85 g (1.3 mol) of zinc powder and 12 g (83 mmol) of finely ground cuprous bromide in 250 ml of anhydrous diethyl ether. The reaction mixture was stirred until its color changed from grey to black (~30 minutes). After addition of 50 g (0.26 mol) of (E)-2-methyl-4-(2,2,3-trimethylcyclopent-3-enyl)but-2-en-1-ol dissolved in 50 ml of the same solvent (Et2O), in 10 minutes (the exothermic reaction triggers a smooth reflux of ether), and 2 drops of TiCl$_4$, stirring at room temperature was continued for further 7 hours. The reaction mixture was then diluted with 300 ml of MTBE, filtered through Celite, the filtrate washed with 200 ml of ice-cold 0.1N HCl and 3×200 ml of brine, dried (MgSO$_4$), concentrated in vacuo and distilled rapidly (0.1 Torr) to give 39 g of a yellowish oil containing 81% of [1-methyl-2-(1,2,2-trimethyl-bicyclo[3.1.0]hex-3-ylmethyl)cyclopropyl]methanol (yield 55%). Further purification by distillation using a 15 cm Vigreux column under 0.08 Torr afforded 27.4 g (48% yield) of olfactorily pure product. GC purity >91%, b.p. 104–105° C./0.08 Torr. More product could be recovered from 4.5 g of rejected (66% pure) fractions.

IR (neat): 3335, 3058, 2952, 2926, 2867, 1463, 1450, 1385, 1362, 1028, 1014 cm$^{-1}$.

Odor: sandalwood, very natural, floral, creamy, powdery, very strong and long-lasting.

EXAMPLE 5

(3"R)-[1-Methyl-2-(1,2,2-trimethylbicyclo[3.1.0]hex-3-ylmethyl)cyclopropyl]-methanol; 2:3 mixture of 2 diastereomers The same reaction conditions as in Example 4 applied to (R,E)-2-methyl-4-(2,2,3-trimethylcyclopent-3-enyl)but-2-en-1-ol, obtained from (R)-(+)-campholenic aldehyde, resulted in a 2:3 mixture of two diastereomers, tentatively (1'R,1"S,2'R,3"R, 5"R)- and (1'S,1"S,2'S,3"R,5"R)-[1-methyl-2-(1,2,2-trimethylbicyclo [3.1.0]hex-3-ylmethyl) cyclopropyl]methanol. $[\alpha]_D^{22}$=+28.5° (c 0.95, ethanol)

Odor: typically sandalwood, very strong and long-lasting

GC-sniff olfactory analysis of this mixture carried out with a DB-FFAP column: peak 1 (first eluted, minor): lactonic, with a sandalwood aspect, peak 2 (major): sandalwood, creamy, warm, strong.

EXAMPLE 6

(3"S)- [1-Methyl-2-(1,2,2-trimethylbicyclo[3.1.0]hex-3-ylmethyl)cyclopropyl]-methanol; 2:3 mixture of 2 diastereomers The same reaction conditions as in Example 4 applied to (S,E)-2-methyl-4-(2,2,3-trimethylcyclopent-3-enyl)but-2-en-1-ol, obtained from (S)-(−)-campholenic aldehyde, resulted in a 2:3 mixture of two diastereomers, tentatively (1'S,1'R,2'S,3"S,5"S)- and (1'R,1"R,2'R,3"S,5"S)-[1-methyl-2-(1,2,2-trimethylbicyclo [3,1,0]hex-3-ylmethyl) cyclopropyl]methanol.

$[\alpha]_D^{22}$=−26.5° (c 0.54, ethanol)

Odor: woody, rosy, sandalwood

GC-sniff olfactory analysis of this mixture carried out as in Example 5: peak 1 (first eluted, minor): floral, rosy, milky, sandalwood, peak 2 (major): lactonic, lily of the valley.

EXAMPLE 7

[1-Ethyl-2-(1,2,2-trimethylbicyclo [3,1,0]hex-3-ylmethyl)cyclopropyl]methanol 20.8 g (0.10 mol) of (E)-2-ethyl-4-(2,2,3-trimethylcyclopent-3-enyl)but-2-en-1-ol was treated according to Example 1 with 52.0 g (0.80 mol) of zinc dust, 8.0 g (81 mmol) of cuprous chloride and 70.0 g (0.40 mol) of dibromomethane except for different sonication time which was 22 hours for the cyclo-propanation step. Flash chromatography of the crude product on silica gel (eluent: hexane/MTBE 4:1) yielded 9.7 g (41% yield) of [1-ethyl-2-(1,2,2-trimethylbicyclo[3.1.0]hex-3-ylmethyl)cyclopropyl] methanol.

IR (neat): 3333, 3058, 2961, 2927, 2869, 1462, 1362, 1033, 1015 cm$^{-1}$.

Odor: sandalwood, fruity, creamy/milk-like, very long-lasting.

EXAMPLE 8

1-[1-Methyl-2-(1,2,2-trimethylbicyclo[3.1.0]hex-3-ylmethyl)cyclopropyl]ethanol 22.0 g (0.34 mol) of zinc powder was added under nitrogen to a vigorously stirred solution of 1.0 g (5.0 mmol) of copper acetate in 80 ml of acetic acid at 90° C. After 5 minutes of stirring at this temperature the red-grey Zn/Cu couple was decanted, washed successively with 20 ml of acetic acid and 3×30 ml of diethyl ether and suspended in 200 ml of diethyl ether. The suspension was treated with a small crystal of iodine and 56.2 g (0.21 mol) of diodomethane and stirring was continued for further 30 minutes. 5.2 g (25 mmol) of (E)-3-methyl-5-(2,2,3-trimethylcyclopent-3-enyl)pent-3-en-2-ol dissolved in 20 ml of diethyl ether was added dropwise and the reaction mixture was heated at reflux for the following 40 hours. The usual treatment (cf. Example 1) yielded 6.8 g of yellow oil which was purified by flash chromatography on silica gel (eluent: hexane/MTBE 4:1) to give 0.9 g (15% yield) of 1-[1-methyl-2-(1,2,2-trimethylbicyclo[3.1.0]hex-3-ylmethyl)cyclopropyl]ethanol.

IR (neat): 3364, 3058, 2955, 2927, 2868, 1463, 1362, 1300, 1100, 1104, 1073, 1015, 931, 901 cm$^{-1}$.

Odor: sandalwood, amber, camphor, minty.

EXAMPLE 9

3-[2-(1,2,2-Trimethylbicyclo[3,1,0]hex-3-yl) cyclopropyl]butan-2-ol 10.4 g (50 mmol) of (E)-3-methyl-5-(2,2,3-trimethylcyclopent-3-enyl)pent-4-en-2-ol was treated according to Example 1 with 17.0 g (0.26 mol) of zinc dust, 2.58 g (26 mmol) of cuprous chloride and 34.6 g (0.13 mol) of diodomethane except for different sonication time which was 46 hours for the cyclopropanation step. Flash chromatography of the crude product on silica gel (eluent: hexane/MTBE 4:1) yielded 7.8 g (64% yield) of 3-[2-(1,2,2-trimethylbicyclo [3.1.0]hex-3-yl)cyclopropyl]butan-2-ol.

IR (neat): 3361, 3059, 2962, 2928, 2869, 1463, 1362, 1091, 1012, 910 cm$^{-1}$.

Odor: floral, woody, dry, fatty, lactonic, rosy.

EXAMPLE 10

[1-Methyl-2-(2,2,3-trimethylcyclopent-3-enylmethyl) cyclopropyl]methanol 2.0 g (12 mmol) of dibromomethane and 3 drops of acetyl bromide were added to the stirred suspension of 9.8 g (0.15 mol) of zinc powder and 1.5 g (10 mmol) of finely ground cuprous bromide in 40 ml of anhydrous diethyl ether. After 30 minutes more stirring at room temperature a solution of 9.7 g (50 mmol) of 2-methyl-4-(2,2,3-trimethylcyclopent-3-enyl)-butan-1-ol in 30 ml of the same solvent was added quickly and stirring at room temperature continued for further 7 hours. During this period more 19.0 g (0.11 mol) of dibromomethane was added in 4 portions. The reaction mixture was filtered and the filtrate washed successively with 100 ml of 1N hydrochloric acid and 100 ml of water, dried (MgSO$_4$) and concentrated in vacuo to give 7.4 g of yellow oil containing 44% of the starting material and 34% of the product. 21.7 g (0.25 mol) of manganese(II) oxide was added to oxidize the former. After 7 hours stirring at room temperature, the reaction mixture was filtered over Celite, the filtrate concentrated in vacuo and the residue purified by flash chromatography on silica gel (eluent: hexane/MTBE 4:1) to give 1.5 g (14% yield) of [1-methyl-2-(2,2,3-trimethyl-cyclopent-3-enylmethyl)cyclopropyl]methanol.

IR (neat): 3346, 3034, 2953, 2928, 2865, 1693, 1463, 1447, 1382, 1359, 1030, 1013, 798 cm$^{-1}$.

Odor: creamy, lactonic, sandalwood.

EXAMPLE 11

1-[2-(2,2,3-Trimethylcyclopent-3-enylmethyl)cyclopropyl]ethanol a) 1-[2-(2,2,3-Trimethylcyclopent-3-enylmethyl)cyclopropyl]ethanone 3.08 g (64 mmol) of 50% oil suspension of sodium hydride was washed with 50 ml of hexane and dried in vacuo. 14.1 g (63 mmol) of trimethylsulfoxonium iodide and 70 ml of dimethyl sulfoxide were successively added at room temperature (ice bath) under nitrogen and with mechanical stirring which was then continued for further 30 minutes. A solution of 10.6 g (55 mmol) of 5-(2,2,3-trimethylcyclopent-3-enyl)pent-3-en-2-one in 30 ml of DMSO was added quickly and the reaction mixture was stirred at room temperature for 2 hours, poured on 200 g of icy 1N aqueous hydrochloric acid and extracted with 200 ml of MTBE. The extract was washed with 2×200 ml of brine, dried (MgSO$_4$) and evaporated in vacuo to give 9.8 g of brown oil which was distilled at 78° C./0.08 Torr and further purified by flash chromatography on silica gel (eluent: hexane/MTBE 7:1) to yield 2.8 g (25% yield) of 1-[2-(2,2,3-trimethyl-cyclopent-3-enylmethyl)cyclopropyl]ethanone.

IR (neat): 3035, 3001, 2955, 2928, 2865, 1699, 1441, 1401, 1360, 1172, 1013, 964, 866, 799 cm$^{-1}$.

Odor: woody, cedar, β-ionone aspect, floral, sandalwood.

b) 1-[2-(2.2.3-Trimethylcyclopent-3-enylmethyl)cyclopropyl]ethanol 1.5 g (7.3 mmol) of 1-[2-(2,2,3-trimethylcyclopent-3-enylmethyl)cyclopropyl]-ethanone dissolved in 5 ml of ethanol was added to a suspension of 0.50 g (13 mmol) of sodium borohydride in 30 ml of the same solvent under nitrogen at 5° C. The reaction mixture was stirred at room temperature for further 2 hours. After addition of 50 ml of 1N aqueous hydrochloric acid it was extracted with 200 ml of MTBE, the organic layer washed with 2×100 ml of brine, dried (MgSO$_4$) evaporated in vacuo and bulb-to-bulb distilled to give 1.3 g of 1-[2-(2,2,3-trimethylcyclopent-3-enylmethyl)cyclopropyl]ethanol (87% yield).

IR (neat): 3352, 3060, 3035, 2955, 2928, 2865, 1652, 1463, 1360, 1106, 1083, 1022, 968, 798 cm$^{-1}$.

Odor: sandalwood, green.

EXAMPLE 12

1-[1-Methyl-2-(2,2,3-trimethylcyclopent-3-enylmethyl)cyclopropyl]ethanol 11.3 g (55 mmol) of 3-methyl-5-(2,2,3-trimethylcyclopent-3-enyl)-pent-3-en-2-one was cyclopropanated with 14.1 g (63 mmol) of trimethylsulfoxonium iodide and 3.08 g (64 mmol) of 50% oil suspension of sodium hydride according to Example 11a giving 5.4 g (45% yield) of 1-[1-methyl-2-(2,2,3-trimethylcyclopent-3-enylmethyl)cyclopropyl]ethanone.

IR (neat): 3035, 2955, 2931, 2865, 2834, 1689, 1463, 1444, 1383, 1359, 1280, 1152, 1139, 1013, 824, 798 cm$^{-1}$.

Odor: woody, dry, anisic, incense.

b) 1- [1-Methyl-2-(2,2,3-trimethylcyclopent-3-enylmethyl)cyclopropyl]ethanol

Sodium borohydride reduction of 3.0 g (13.6 mmol) of 1-[1-methyl-2-(2,2,3-trimethyl-cyclopent-3-enylmethyl)cyclopropyl]ethanone from Example 12a according to Example 11b gave 1.6 g of 1-[1-methyl-2-(2,2,3-trimethylcyclopent-3-enylmethyl)cyclopropyl]ethanol (53% yield).

IR (neat): 3366, 3055, 3035, 2955, 2929, 2865, 2834, 1463, 1382, 1359, 1303, 1107, 1075, 1045, 1012, 902, 930, 799 cm$^{-1}$.

Odor: sandalwood, slightly phenolic.

EXAMPLE 13

1-(2,2,3-Trimethylcyclopent-3-enylmethylspiro[2,4]heptan-4-ol a) 1-(2,2,3-Trimethylcyclopent-3-enylmethyl)spiro[2,4]heptan-4-one 13.0 g (60 mmol) of 2-[2-(2,2,3-trimethylcyclopent-3-enyl)ethylidene]cyclopentanone was cyclopropanated with 16.2 g (74 mmol) of trimethylsulfoxonium iodide and 3.6 g (75 mmol) of 50% oil suspension of sodium hydride according to Example 11a to give 4.9 g (35% yield) of 1-(2,2,3-trimethylcyclopent-3-enylmethyl)spiro[2.4]heptan-4-one.

IR (neat): 3035, 2956, 2929, 2865, 1726, 1437, 1390, 1360, 1257, 1170, 1118, 1013, 798 cm$^{-1}$.

Odor: woody, cedar, camphor/earthy.

b) 1-(2,2,3-Trimethylcyclopent-3-enylmethyl)spiro[2.4]heptan-4-ol

Sodium borohydride reduction of 3.8 g (16 mmol) of 1-(2,2,3-trimethylcyclopent-3-enylmethyl)spiro[2.4]heptan-4-one according to Example 11b gave 2.3 g of 1-(2,2,3-trimethylcyclopent-3-enylmethyl)spiro[2,4]heptan-4-ol (61% yield).

IR (neat): 3361, 3036, 2954, 2930, 2865, 1652, 1444, 1382, 1359, 1080, 1023, 1012, 960, 798 cm$^{-1}$.

Odor: sandalwood, milky, green, sweet.

EXAMPLE 14

(1,2,2-Trimethylbicyclo [3.1.0]hex-3-yl)ethanal a) 2-(1,2,2-Trimethylbicyclo[3.1.0]hex-3-ylmethyl)-[1,3]dioxolane 150 ml (0.15 mol) of 1.0 M solution of diethylzinc in hexane was added to 500 ml of 1,2-dichloroethane under nitrogen. After having added 66.0 g (0.23 mol) of diiodomethane, while maintaining the temperature at 15–20° C. (ice bath), the solution was stirred at room temperature for 30 minutes, then 20.0 g ( 0.10 mol) of 2-(2,2,3-trimethylcyclopent-3-enylmethyl)-[1,3]dioxolane was added dropwise at 25° C. and the stirring continued for three hours. The reaction mixture was treated with 100 ml of 20% aqueous potassium carbonate, the organic layer separated and the aqueous layer extracted with diethyl ether. The combined organic phases were dried (MgSO$_4$) and evaporated in vacuo. 22 g of the crude product was distilled at 95° C./0.1 Torr to give 14.9 g (71% yield) of 2-(1,2,2-trimethylbicyclo[3.1.0]hex-3-ylmethyl)-[1,3]dioxolane used in the next step without further purification b) (1,2,2-trimethylbicyclo[3,1,0]hex-3-yl)ethanal A mixture of 11.0 g (52 mmol) of 2-(1,2,2-trimethylbicyclo[3.1.0]hex-3-ylmethyl)-[1,3]-dioxolane, 80 ml of acetone, 40 ml of water, 1.5 ml of conc. hydrochloric acid and 10 g of silica gel was stirred at reflux for 4 hours. After filtration, the solution was diluted with diethyl ether, washed with water, dried (MgSO$_4$) and evaporated in vacuo. Kugelrohr distillation of the residue gave 6.8 g (79% yield) of (1,2,2-trimethylbicyclo[3,1,0]hex-3-yl)ethanal.

IR (neat): 3061, 3000, 2956, 2929, 2869, 2717, 1726, 1464, 1365, 1018 cm$^{-1}$.

Odor: green, ketonic, bitter.

EXAMPLE 15

2-Methyl-4-(1,2,2-trimethylbicyclo[3.1.0]hex-3-yl)but-2-enal 30 g (0.18 mol) of (1,2,2-trimethylbicyclo[3.1.0]hex-3-yl)ethanal was added to 5.0 ml (24 mmol) of stirred 5.4 M methanolic solution of sodium methylate diluted with 40 ml of methanol. 35 g (0.61 mol) of propionaldehyde was added at 25° C. with cooling during 10 minutes, the reaction mixture stirred at room temperature for 1.5 hours, neutralized with acetic acid and the solvent removed in vacuo. The residue was dissolved in 100 ml of ether, washed with 3×80 ml of water, dried (MgSO$_4$) and evaporated in vacuo. Purification by Kugelrohr distillation at 94° C./0.1 Torr followed by flash chromatography on silica gel (eluent: hexane/MTBE 4:1) gave 16.0 g (43% yield) of 2-methyl-4-(1,2,2-trimethylbicyclo[3.1.0]hex-3-yl)but-2-enal.

IR (neat): 3060, 2998, 2954, 2927, 2868, 1690, 1644, 1463, 1451, 1363, 1014 cm$^{-1}$.

Odor: woody, fatty, sandalwood.

EXAMPLE 16

2-Methyl-4-(1,2,2-trimethylbicyclo [3,1,0]hex-3-yl)but-2-en-1-ol 0.5 g (10 mmol) of sodium borohydride dissolved in 5 ml of water was added portionwise to the solution of 5.0 g (24 mmol) of 2-methyl-4-(1,2,2-trimethylbicyclo[3.1.0]hex-3-yl)but-2-enal in 20 ml of ethanol maintained at 0° C. Stirring was continued for 1 hour at 0–5° C., then acetone was added to destroy the excess of hydride. The reaction mixture was poured on 100 ml of water, extracted with 2×100 ml of ether, dried (MgSO$_4$) and evaporated in vacuo. Kugelrohr distillation of the residue at 160° C./0.1 Torr gave 4.5 g (90% yield) of 2-methyl-4-(1,2,2-trimethylbicyclo[3.1.0]hex-3-yl)but-2-en-1-ol.

IR (neat): 3312, 3059, 2998, 2951, 2927, 2867, 1463, 1386, 1362, 1074, 1013 cm$^{-1}$.

Odor: woody, sandalwood, slightly camphor.

EXAMPLE 17

2-Ethyl-4-(1,2,2-trimethylbicyclo[3.1.0]hex-3-yl)but-2-enal

The condensation of 20.0 g (0.12 mol) of (1,2,2-trimethylbicyclo[3.1.0]hex-3-yl)ethanal with 17.0 g (0.24 mol) of butyraldehyde catalyzed with sodium ethoxide prepared from 0.25 g of sodium in 35 ml of ethanol, according to Example 15, gave 9.98 g (38% yield) of 2-ethyl-4-(1,2,2-trimethylbicyclo[3.1.0]hex-3-yl)but-2-enal.

IR (neat): 3060, 2963, 2870, 2711, 1738, 1689, 1641, 1463, 1364, 1151, 1065, 1014, 798 cm$^{-1}$.

Odor: fatty, lactonic, green, sandalwood.

EXAMPLE 18

2-Ethyl-4-(1,2,2-trimethylbicyclo[3 1.0]hex-3-yl)but-2-en-1-ol

Sodium borohydride reduction of 10.0 g (45 mmol) of 2-ethyl-4-(1,2,2-trimethylbicyclo[3.1.0]hex-3-yl)but-2-enal as in Example 16 gave 6.1 g (64% yield) of 2-ethyl-4-(1,2,2-trimethylbicyclo[3.1.0]hex-3-yl)but-2-en-1-ol.

IR (neat): 3316, 3061, 3000, 2962, 2930, 2869, 1709, 1463, 1363, 1299, 1045, 1013 cm$^{-1}$.

Odor: woody, cedar, sandalwood.

EXAMPLE 19

3-Methyl-5-(1,2,2-trimethylbicyclo[3.1.0]hex-3-yl)pent-3-en-2-one 560 g (8.5 mol) of butan-2-one and 234 g (1.4 mol) of (1,2,2-trimethyl-bicyclo[3.1.0]hex-3-yl)ethanal were added to 48 g (0.75 mol) of potassium hydroxide dissolved in 500 ml of water and 1.4 l of methanol. The reaction mixture was stirred overnight with ice-bath cooling, poured into 3 l of water and extracted with diethyl ether. The extract was washed with water, dried (MgSO$_4$) and evaporated in vacuo. The residue was distilled at 108° C./0.1 Torr to give 140 g (45% yield) of 3-methyl-5-(1,2,2-trimethylbicyclo[.,1.0]hex-3-yl)pent-3-en-2-one.

IR (neat): 3060, 2999, 2954, 2927, 2868, 1670, 1641, 1463, 1364, 1287, 1088, 1014 cm$^{-1}$.

Odor: woody, lactonic, fatty, sandalwood.

EXAMPLE 20

3-Methyl-5-(1,2,2-trimethylbicyclo[3.1.0]hex-3-yl)pent-3-en-2-ol 0.37 g (10 mmol) of sodium borohydride was added portionwise with cooling to the solution of 3.7 g (10 mmol) of cerium trichloride and 2.0 g (10 mmol) of 3-methyl-5-(1,2,2-trimethylbicyclo[3.1.0]hex-3-yl)pent-3-en-2-one in 25 ml of methanol. After 5 more minutes water was added and the mixture extracted with diethyl ether, dried (MgSO$_4$) and evaporated in vacuo. Purification by flash. chromatography on silica gel (eluent: hexane/MTBE 9:1) gave 1.3 g (58% yield) of 3-methyl-5-(1,2,2-trimethylbicyclo [3.1.0] hex-3-yl)pent-3-en-2-ol.

IR (neat): 3340, 3059, 2998, 2963, 2928, 2868, 1463, 1363, 1298, 1079, 1013, 892 cm$^{-1}$.

Odor: sandalwood, natural, green, lactonic.

EXAMPLE 21

3-Methyl-5-(1,2,2-trimethylbicyclo[3,1,0]hex-3-yl)pent-4-en-2-one 66.0 g of potassium tert-butoxide dissolved in 850 ml of tetrahydrofuran was added to the solution of 140 g (0.64 mol; 70% pure) of 3-methyl-5-(1,2,2-trimethylbicyclo-[3.1.0]hex-3-yl)pent-3-en-2-one in 850 ml of the same solvent at 0° C. After 30 minutes of stirring at room temperature the reaction mixture was poured on 1 l of aqueous ammonium chloride solution. After the usual workup the crude product was purified by flash chromatography on silica gel (eluent: hexane/MTBE 19:1) to give three fractions: 5.1, 28.1 and 22.3 g containing respectively 36, 78, and 92% of 3-methyl-5-(1,2,2-trimethylbicyclo[3.1.0]hex-3-yl)pent-4-en-2-one (~40% yield).

IR (neat): 3059, 2958, 2929, 2868, 1715, 1452, 1361, 1166, 1013, 976 cm$^{-1}$.

Odor: slightly cedar, tobacco.

EXAMPLE 22

3-Methyl-5-(1,2,2-trimethylbicyclo [3.1.0]hex-3-yl)pent-4-en-2-ol 2.2 g (10 mmol) of 3-methyl-5-(1,2,2-trimethylbicyclo [3.1.0]hex-3-yl)pent-4-en-2-one was reduced as in Example 16 to give 1.9 g (85% yield) of 3-methyl-5-(1,2,2-trimethylbicyclo[3.1.0]hex-3-yl)pent-4-en-2-ol.

IR (neat): 3360, 3058, 2998, 2962, 2927, 2868, 1451, 1362, 1091, 1012, 976 cm$^{-1}$.

Odor: sandalwood, floral.

EXAMPLE 23

3,3-Dimethyl-5-(1,2,2-trimethylbicyclo[3.1.0]hex-3-yl)pent-4-en-2-one 5.0 g (43 mmol) of potassium tert-butoxide dissolved in 50 ml of tetrahydrofuran was added to the solution of 8.7 g (40 mmol) of 3-methyl-5-(1,2,2-trimethylbicyclo-[3.1.0] hex-3-yl)pent-3-en-2-one in 50 ml of the same solvent at −40° C. After 5 minutes of stirring at −35° C. 7.0 g (45 mmol) of methyl iodide was added rapidly and stirring continued at −20° C. for 10 minutes. The reaction mixture was poured on 200 ml of water and worked up as usual. Flash chromatography of the crude product (silica gel; eluent: hexane/MTBE 9:1) followed by Kugelrohr distillation at 150° C./0.1 Torr gave 7.3 g (78% yield) of 3,3-dimethyl-5-(1,2,2-trimethylbicyclo[3.1.0]hex-3-yl)pent-4-en-2-one.

IR (neat): 3036, 2955, 2930, 2864, 2841, 1711, 1463, 1444, 1382, 1359, 1122, 979, 797 cm$^{-1}$.

Odor: woody, musty.

EXAMPLE 24

3,3-Dimethyl-5-(1,2,2-trimethylbicyclo[3.1.0]hex-3-yl) pent-4-en-2-ol 6.5 g (28 mmol) of 3,3-dimethyl-5-(1,2,2-trimethylbicyclo[3.1.0]hex-3-yl)pent-4-en-2-one was reduced as in Example 16 to give 6.0 g (92% yield) of 3,3-dimethyl-5-(1,2,2-trimethylbicyclo[3.1.0]hex-3-yl)pent-4-en-2-ol.

IR (neat): 3396, 3035, 2955, 2931, 2865, 2840, 1462, 1381, 1359, 1100, 981, 910, 797 cm$^{-1}$.

Odor: sandalwood, woody.

EXAMPLE 25

5-(1,2,2-Trimethylbicyclo[3,1,0]hex-3-yl)pent-4-en-2-ol and 1-[2-(1,2,2-Trimethylbicyclo[3.1.0]hex-3-yl) cyclopropyl]propan-2-ol a) Acetic acid 5-(2,2,3-trimethylcyclopent-3-enyl)pent-4-en-2-yl ester 50 g (0.48 mol) of acetic anhydride was added dropwise to the solution of 78.6 g (0.40 mol) of 5-(2,2,3-trimethylcyclopent-3-enyl)pent-4-en-2-ol and 5.0 g of 4-dimethylaminopyridine in 150 ml of MTBE. The reaction mixture was stirred at 50–55° C. for 1 hour, treated with 0.5 l of water and extracted with 3×150 ml of hexane. The combined organic layers were neutralized with aqueous potassium hydrogen carbonate solution, washed with water, dried (MgSO$_4$) and evaporated in vacuo. The residue (102 g) was distilled at 80–81° C./0.2 Torr to give 89.8 g (95% yield) of acetic acid 5-(2,2,3-trimethyl-cyclopent-3-enyl)pent-4-en-2-yl ester.

b) Acetic acid 5-(1,2,2-trimethylbicyclo[3.1.0]hex-3-yl) pent-4-en-2-yl ester and Acetic acid 1-[2-(1,2,2-trimethylbicyclo[3,1,0]hex-3-yl)cyclopropyl]propan-2-yl ester 30 g (0.17 mol) of dibromomethane was added dropwise under nitrogen to the suspension of 100 g (1.5 mol) of zinc powder and 15 g (0.10 mol) of cuprous bromide in 700 ml of diethyl ether. 1 ml of acetyl bromide was added and the reaction mixture was stirred for 30 minutes before addition of 59 g (0.25 mol) of the acetate prepared in a). 250 ml (1.44 mol) of dibromomethane was then added dropwise during 6.5 hours and stirring was continued for 1.5 hours at 40° C. After the usual work-up, 69 g of crude product was fractionated on a 25 cm packed column at 0.1 Torr:

fraction 1 b.p. 76–80° C.: 7.2 g and fraction 2 b.p. 80–83° C.: 24.5 g containing respectively 60 and 81% of acetic acid 5-(1,2,2-trimethylbicyclo[3.1.0] hex-3-yl)pent-4-en-2-yl ester;

fraction 3 b.p. 87–102° C.: 11.3 g of acetic acid 1-[2-(1, 2,2-trimethylbicyclo[3.1.0]hex-3-yl)cyclopropyl]propan-2-yl ester.

c) 5-(1,2,2-Trimethylbicyclo [3.1.0]hex-3-yl)pent-4-en-2-ol

Fraction 2 of Example 25b was hydrolized with 9.8 g of potassium hydroxide in 130 ml of methanol and 10 ml of water at 45–65° C. for 1 hour. The reaction mixture was neutralized with conc. citric acid and extracted with diethyl ether. After the usual work-up the crude product was distilled (Kugelrohr) at 150° C./0.1 Torr to give 20 g (98% yield) of 5-(1,2,2-trimethylbicyclo[3.1.0]hex-3-yl)pent-4-en-2-ol.

IR (neat): 3344, 3059, 2999, 2962, 2926, 2867, 1463, 1362, 1126, 1075, 1013, 975, 942 cm$^{-1}$.

Odor: woody, cedar, sandalwood aspect, camphor.

d) 1-[2-(1,2,2-Trimethylbicyclo[3.1.0]hex-3-yl) cyclopropyl]propan-2-ol

Fraction 3 of Example 25b was hydrolized according to the same reaction conditions as in Example 25c to give 1-[2-(1,2,2-trimethylbicyclo[3.1.0]hex-3-yl)cyclopropyl] propan-2-ol in 97% yield.

IR (neat): 3347, 3059, 2998, 2962, 2926, 2868, 1464, 1362, 1127, 1090, 1012, 949 cm$^{-1}$.

Odor: woody, dry, amber.

EXAMPLE 26

[1,2-Dimethyl-2-(1,2,2-trimethylbicyclo[3,1,0]hex-3-ylmethyl)cyclopropyl]methanol a) 2.3-Dimethyl-4-(2,2,3-trimethylcyclopent-3-enyl)but-2-enoic acid ethyl ester 47.6 g (0.20 mol) of triethyl 2-phosphonopropionate was added dropwise under nitrogen to a cooled and stirred suspension of 4.8 g (0.20 mol) of sodium hydride in 300 ml of THF and stirring continued for 30 min. at room temperature. After addition of 30 g (0.18 mol) of 1-(2,2,3-trimethylcyclopent-3-enyl)propan-2-one, prepared from campholenic aldehyde as known per se, and 46 hours of more stirring, the reaction mixture was poured into 400 ml of ice-cold 1N hydrochloric acid and extracted with 2×300 ml of MTBE. The extract was washed with 5×350 ml of brine, dried (MgSO$_4$) and concentrated in vacuo. The distillation at 90–97° C./0.065–0.075 Torr yielded 13 g of the product which was further purified by flash chromatography on silica gel (eluent: hexane/MTBE 15:1) to give 6.4 g (14% yield) of 2,3-dimethyl-4-(2,2,3-trimethylcyclopent-3-enyl)but-2-enoic acid ethyl ester.

IR (neat): 3036, 2955, 2932, 2866, 1714, 1630, 1462, 1445, 1361, 1282, 1247, 1206, 1095, 1031, 798, 771 cm$^{-1}$.

b) 2.3-Dimethyl-4-(2,2,3-trimethylcyclopent-3-enyl)but-2-en-1-ol 5.3 g (21 mmol) of the ester obtained in a), diluted with 50 ml of anhydrous diethyl ether, was added to a stirred suspension of 0.8 g (21 mmol) of lithium aluminium hydride in 70 ml of the same solvent and the reaction mixture was refluxed for 4 hours. 1.5 ml of water, 1.5 ml of 15% aqueous sodium hydroxide solution and again 1.5 ml of water was successively added at room temperature. After filtration and extraction with 2×250 ml of MTBE, the combined organic phases were washed with 100 ml of 2M sodium hydroxide solution and 2×100 ml of brine, dried (MgSO4) and concentrated in vacuo to give 4.4 g (quantitative yield) of 2,3-dimethyl-4-(2,2,3-trimethylcyclopent-3-enyl)but-2-en-1-ol. The product was used in the next step without further purification.

IR (neat): 3325, 3036, 2954, 2930, 2865, 1653, 1445, 1381, 1360, 1011, 798 cm$^{-1}$.

c) [1,2-Dimethyl-2-(1,2,2-trimethylbicyclo[3.1.0]hex-3-ylmethyl)cyclo-propyl]methanol 4.0 g (19 mmol) of the alcohol of b) was cyclopropanated according to Example 1 with 9.8 g (150 mmol) of zinc powder, 1.48 g (15 mmol) of cuprous chloride and 26.8 g (100 mmol) of methylene iodide except for the shorter reaction time, namely 2 hours. After repeated flash chromatography on silica gel (eluent: hexane/MTBE 5:1) of the crude product, a sample of 0.26 g (6%) of olfactorily pure [1,2-dimethyl-2-(1,2,2-trimethylbicyclo [3.1.0]hex-3-ylmethyl)cyclopropyl]methanol was obtained.

IR (neat): 3352, 3058, 2953, 2929, 2869, 1463, 1452, 1379, 1363, 1087, 1029, 1014 cm$^{-1}$.

Odor: Woody, sandalwood, lactonic, warm, musky.

EXAMPLE 27

[1-Methyl-2-[1-(1,2,2-trimethylbicyclo[3.1.0]hex-3-yl)ethyl]cyclopropyl]methanol a) 2-Methyl-4-(2,2,3-trimethylcyclopent-3-enyl)pent-2-enal 60.0 g (0.36 mol) of 2-(2,2,3-trimethylcyclopent-3-enyl)propionaldehyde, prepared from campholenic aldehyde as known per se, and 42.0 g (0.72 mol) of propanal was added successively during 15 min and 2 hours, respectively, to the sodium methylate solution prepared from 0.83 g of sodium and 200 ml of anhydrous methanol, at 10° C. The reaction mixture was stirred at 10° C. for 2 hours and at room temperature for the following 42 hours. After addition of 5 ml of acetic acid the solvent was evaporated in vacuo at the temperature maintained below 50° C. The residue was diluted with 500 ml of MTBE, washed with 2×200 ml of brine, dried (MgSO$_4$), concentrated in vacuo and distilled at 76–95° C./0.1 Torr to give 28.1 g (38%) of 2-methyl-4-(2,2,3-trimethylcyclopent-3-enyl)pent-2-enal. An analytical sample was prepared by flash chromatography on silica gel (eluent: hexane/MTBE 12:1).

IR (neat): 3039, 2960, 2934, 2872, 2702, 1725, 1458, 1386, 1362, 1118, 1025, 806 cm$^{-1}$.

b) 2-Methyl-4-(2,2,3-trimethylcyclopent-3-enyl)pent-2-en-1-ol 10.0 g (48 mmol) of 2-methyl-4-(2,2,3-trimethylcyclopent-3-enyl)pent-2-enal was reduced according to the procedure of Example 11b) to give, after distillation at 91° C./0.09 Torr, 6.5 g (65%) of 2-methyl-4-(2,2,3-trimethylcyclopent-3-enyl)pent-2-en-1-ol.

IR (neat): 3323, 3035, 2956, 2929, 2867, 2833, 1658, 1445, 1382, 1358, 1063, 1010, 871, 802 cm$^{-1}$.

c) [1-Methyl-2-[1-(1,2,2-trimethylbicyclo[3,1,0]hex-3-yl)ethyl]cyclopropyl]methanol A solution of 5.15 g (25 mmol) of the alcohol of Example 27b in 20 ml of diethyl ether was added rapidly to the Zn/Cu couple prepared by 15 min sonication of the suspension of 13.0 g (200 mmol) of zinc powder, 2.0 g (20 mmol) of cuprous chloride and 5.0 g (19 mmol) of methylene iodide in 30 ml of the same solvent. 21.8 g (81 mmol) more of methylene iodide was added dropwise during 4 hours and stirring at 30° C. was continued for 2 more hours. The reaction mixture was diluted with 200 ml of diethyl ether, filtered through Celite, washed with 150 ml of ice-cold 1N hydrochloric acid and 2×100 ml of brine, dried (MgSO$_4$) and concentrated in vacuo. 6.8 g of the crude product was purified by flash chromatography on silica gel (eluent: hexane/MTBE 4:1) to give 1.25 g (21% yield) of [1-methyl-2-[1-(1,2,2-trimethylbicyclo[3.1.0]hex-3-yl)ethyl]cyclopropyl]methanol.

IR (neat): 3345, 3058, 2955, 2929, 2869, 1450, 1382, 1362, 1030, 1017, 980, 866, 833 cm$^{-1}$.

Odor: Sandalwood, creamy, lactonic, tobacco, woody.

EXAMPLE 28

Fresh - Floral -Woody Accord for consumer goods

| | parts per weight |
|---|---|
| Aldehyde C12 MNA | 0.3 |
| Aldehyde iso C11 | 0.7 |
| cis-Jasmone | 1 |
| 3-cis-Hexenol | 3 |

-continued

Fresh - Floral -Woody Accord for consumer goods

| | parts per weight | |
|---|---|---|
| Eucalyptus globulus oil China | 5 | |
| Undecavertol | 5 | |
| Stemone | 5 | |
| Rose oxyde | 5 | |
| Nonadyl | 10 | |
| Viridine | 10 | |
| Anther | 10 | |
| Geranyl acetate | 15 | |
| Iso E super | 20 | |
| Allyl cyclohexylpropionate | 20 | |
| Dihydro myrcenol | 30 | |
| β-Ionone synt. | 30 | |
| Citronellol | 40 | |
| Verdyl propionate | 40 | |
| α,α-Dimethylphenethyl acetate | 40 | |
| Agrumex | 50 | |
| Lilial | 60 | |
| Isoraldeine 70 | 70 | |
| Fixolide | 70 | |
| Bergamot oil | 80 | |
| Verdyl acetate | 80 | |
| p-tert-Butylcyclohexyl acetate | 100 | |
| Hexylcinnamic aldehyde | 150 | |
| Compound of Example 4 | 10 | |
| Dipropylene glycol | 40 | 50 |
| Total | 1000 | 1000 |

The novel compound gives to the accord a creamy, sweet, rich sandalwood effect and increases the volume and the substantivity of the perfume composition.

EXAMPLE 29

Floral -Ambery Feminine Accord

| | parts per weight | |
|---|---|---|
| Cardamone oil Ceylon | 2 | |
| Indolene 10% DPG | 3 | |
| Stemone | 3 | |
| Aldehyde C11 10% DPG | 3 | |
| Allyl amyl glycolate | 4 | |
| Cassione (4-Benzo-1,3-dioxo-5-yl-but-2-one) 10% DPG | 5 | |
| Coumarine | 5 | |
| Citronellyl acetate | 5 | |
| Cyclal C 10% DPG | 5 | |
| cis-Jasmone 10% DPG | 6 | |
| Geraniol pure | 8 | |
| Benzyl acetate | 10 | |
| Benzyl salicylate | 20 | |
| Patchouli oil | 25 | |
| Vanillin | 25 | |
| 3-cis-Hexenyl salicylate | 30 | |
| Linalyl acetate | 40 | |
| Iso E super | 40 | |
| Phenyl ethyl alcohol | 45 | |
| Mandarin oil (reconstitution) | 50 | |
| Linalool | 60 | |
| Bergamot oil | 80 | |
| Galaxolide 50% DEP | 200 | |
| Hedione | 210 | |
| Compound of Example 4 | 10 | |
| Dipropylene glycol | 106 | 116 |
| | 1000 | 1000 |

The novel compound gives to the accord a creamy, sweet, rich sandalwood effect and increases the volume and the substantivity of the perfume composition.

For the exact definition of the trivial names mentioned above, see Flavour and Fragrance Materials 1995, Allured Publishing Co., Carol Stream, Ill. 60188-2787, USA.

We claim:
1. A compound of the formula

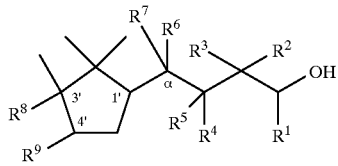

in which $R^1$ to $R^7$ are, independently, H, methyl or ethyl, $R^8+R^9$ together form methylene (—$CH_2$—) or a single bond, or $R^1+R^2$ together form ($CH_2$)$_n$—, with n being 3 or 4, or $R^3+R^5$ or $R^5+R^7$ together form methylene or a single bond; and the presence of at least one cyclopropane ring in the molecule is compulsory and the side chain can be saturated or contains one double bond in position $\alpha,\beta$ or $\beta,\gamma$.

2. 3-Methyl-5-(1,2,2-trimethylbicyclo[3.1.0]hex-3-yl)pentan-2-ol.

3. 2,3-Dimethyl-4-( 1,2,2-trimethylbicyclo[3.1.0]hex-3-yl)butan-1-ol.

4. 3,3-Dimethyl-5-(1,2,2-trimethylbicyclo[3.1.0]hex-3-yl)pentan-2-ol.

5. [1-Methyl-2-(1,2,2-trimethylbicyclo[3.1.0]hex-3-ylmethyl)cyclopropyl]methanol.

6. (3"R)-[1-Methyl-2-(1,2,2-trimethylbicyclo[3.1.0]hex-3-ylmethyl)cyclopropyl]methanol.

7. (3"S)-[1-Methyl-2-(1,2,2-trimethylbicyclo[3.1.0]hex-3-ylmethyl)cyclopropyl]methanol.

8. [1-Ethyl-2-(1,2,2-trimethylbicyclo[3.1.0]hex-3-ylmethyl)cyclopropyl]methanol.

9. 1-[1-Methyl-2-(1,2,2-trimethylbicyclo[3.1.0]hex-3-ylmethyl)cyclopropyl]ethanol.

10. 3- [2-(1,2,2-Trimethylbicyclo [3.1.0]hex-3-yl)cyclopropyl]butan-2-ol.

11. [1-Methyl-2-(2,2,3-trimethylcyclopent-3-enylmethyl)cyclopropyl]methanol.

12. 1-[2-(2,2,3-Trimethylcyclopent-3-enylmethyl)cyclopropyl]ethanol.

13. 1- [1-Methyl-2-(2,2,3-trimethylcyclopent-3-enylmethyl)cyclopropyl]ethanol.

14. 1-(2,2,3-Trimethylcyclopent-3-enylmethyl)spiro [2.4] heptan-4-ol.

15. 2-Methyl-4-( 1,2,2-trimethylbicyclo[3.1.0]hex-3-yl)but-2-en-1-ol.

16. 2-Ethyl-4-( 1,2,2-trimethylbicyclo[3.1.0]hex-3-yl)but-2-en-1-ol.

17. 3-Methyl-5-( 1,2,2-trimethylbicyclo[3.1.0]hex-3-yl)pent-3-en-2-ol.

18. 3-Methyl-5-(1,2,2-trimethylbicyclo[3.1.0]hex-3-yl)pent-4-en-2-ol.

19. 3,3-Dimethyl-5-( 1,2,2-trimethylbicyclo [3.1.0]hex-3-yl)pent-4-en-2-ol.

20. 5-(1,2,2-Trimethylbicyclo[3.1.0]hex-3- yl)pent-4-en-2-ol.

21. 1-[2-(1,2,2-Trimethylbicyclo [3.1.0]hex-3-yl)cyclopropyl]propan-2-ol.

22. [1,2-Dimethyl-2-(1,2,2-trimethylbicyclo[3.1.0]hex-3-ylmethyl)cyclopropyl]methanol.

23. [1-Methyl-2-[1-( 1,2,2-trimethylbicyclo[3.1.0]hex-3-yl)ethyl]cyclopropyl]methanol.

24. An odorant composition containing at least one of the compounds according to claim 1 and an odorant acceptable carrier.

* * * * *